(12) United States Patent
Heiler

(10) Patent No.: US 7,897,553 B2
(45) Date of Patent: Mar. 1, 2011

(54) BIGUANIDE COMPOSITION WITH LOW TERMINAL AMINE

(75) Inventor: David J. Heiler, Avon, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 655 days.

(21) Appl. No.: 11/865,746

(22) Filed: Oct. 2, 2007

(65) Prior Publication Data

US 2008/0261841 A1   Oct. 23, 2008

Related U.S. Application Data

(60) Provisional application No. 60/853,579, filed on Oct. 23, 2006, provisional application No. 60/895,770, filed on Mar. 20, 2007.

(51) Int. Cl.
C11D 3/26 (2006.01)
C11D 3/30 (2006.01)
C11D 3/37 (2006.01)

(52) U.S. Cl. ............ 510/112; 510/383; 510/384; 510/499; 510/504; 424/78.04

(58) Field of Classification Search ........... 510/112, 510/383, 384, 499, 504; 424/78.04
See application file for complete search history.

(56) References Cited

U.S. PATENT DOCUMENTS

| 3,428,576 A | 2/1969 | Dickinson et al. |
| 4,758,595 A | 7/1988 | Ogunbiyi et al. |
| 5,965,088 A | 10/1999 | Lever |
| 6,121,327 A | 9/2000 | Tsuzuki et al. |
| 6,143,799 A | 11/2000 | Chowhan et al. |
| 2003/0032768 A1 | 2/2003 | Stockel |
| 2004/0127372 A1* | 7/2004 | Ketelson et al. ............ 510/112 |

FOREIGN PATENT DOCUMENTS

| EP | 701821 | 3/1996 |
| EP | 788797 | 9/1997 |
| GB | 1434040 | 4/1976 |
| WO | WO 98/20738 A | 5/1998 |

OTHER PUBLICATIONS

International Search Report and Written Opinion dated Apr. 24, 2008.

* cited by examiner

*Primary Examiner*—Gregory R Del Cotto
(74) *Attorney, Agent, or Firm*—Joseph Barrera

(57) ABSTRACT

A polymeric biguanide composition comprising less than 18 mol % of terminal amine groups as measured by $^{13}$C NMR. The polymeric biguanide composition also is characterized by a relative increase in the molar concentration of terminal guanidine groups or terminal cyanoguanidino groups. The invention is also directed to ophthalmic compositions comprising the polymeric biguanide compositions. The polymeric biguanide compositions can be used as an antimicrobial component in an ophthalmic lens care solution, or as a preservative to in a pharmaceutical composition or other health care product.

24 Claims, 2 Drawing Sheets

BIGUANIDE COMPOSITION WITH LOW TERMINAL AMINE

This application claims the benefit of Provisional Patent Application No. 60/853,579 filed Oct. 23, 2006 and Provisional Patent Application No.: 60/895,770 filed Mar. 20, 2007, and they are incorporated herein by reference.

The present invention relates to a polymeric biguanide composition, and the use of the polymeric biguanide composition as an antimicrobial component.

BACKGROUND OF THE INVENTION

Biguanides, including polymeric biguanides, as a class are known to have antimicrobial activity. Poly(hexamethylene biguanide) also known as PHMB or PAPB has been used as an antimicrobial component in many applications including topical disinfectants and as a preservative in health care products. PHMB is commonly represented by the following formula, though it is known to exist as a complex mixture of polymeric biguanides with various terminal groups including guanidine (not shown).

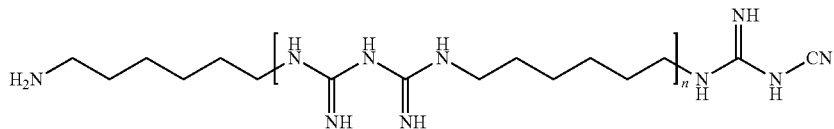
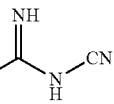

The value n represents the number of repeating units of the biguanide polymer. GB 1434040 describes the use of PHMB and several other biguanide structures and their effectiveness as antimicrobial components.

PHMB has been used in ophthalmic compositions, e.g., in contact, lens care solutions. Ophthalmic lens care solutions that contain PHMB represent a significant improvement in patient comfort and antimicrobial effectiveness compared to most other antimicrobial components. However, as with any antimicrobial component there remains a tradeoff between the concentration of the antimicrobial component in the solution and the comfort experienced by the patient. Due to its wide commercial acceptance, extensive efforts have been made to improve the antimicrobial efficacy or the comfort level to the patient by chemically modifying PHMB. For example, many derivatives of PHMB have been reported that alter the length of the alkylene group, place substituents on the alkylene repeating unit, change the length of the polymer, i.e., molecular weight or n, or modify the terminal groups.

EP701821 describes a biguanide derivative having 1 to 500 polymeric repeat units that is formulated with a phosphoric acid and phosphoric acid salt. EP788797 describes the use of PHMB having a molecular weight of less than 5000 Da, e.g., 3000 Da to 4000 Da for treatment of urogenital disease and parasites of the abdominal cavity.

U.S. Pat. No. 6,121,327 describes a PHMB derivative in which the amino terminal groups are replaced by amido groups, RC(O)NH—. The R group can include alkyls, cycloalkyls, polyethyleneoxides and polypropyleneoxides. In the case of poly(ethyl)propylene oxides, the added surfactant character is said to provide good efficacy and lower toxicity.

There remains an interest and need for an improved antimicrobial biguanide composition that offers a greater comfort level to the patient without sacrificing antimicrobial efficacy.

SUMMARY OF THE INVENTION

The invention is directed to a polymeric biguanide composition comprising less than 18 mol % of terminal amine groups as measured by $^{13}$C NMR. The polymeric biguanide composition also is characterized by a relative increase in the molar concentration of terminal guanidine groups or terminal cyanoguanidino groups. For example, in one embodiment, the biguanide composition comprises less than 18 mol % of terminal amine groups, and 55 mol % or greater of terminal guanidine groups, as measured by $^{13}$C NMR. In another embodiment, the biguanide composition comprises less than 18 mol % of terminal amine groups, 40 mol % or greater of terminal cyanoguanidino groups and less than 50 mol % of terminal guanidine groups, as measured by $^{13}$C NMR.

The invention is also directed to ophthalmic compositions comprising the polymeric biguanide compositions. For example, the polymeric biguanide compositions can be used as an antimicrobial component in an ophthalmic lens care solution, or as a preservative in a pharmaceutical composition.

The invention is also directed to a process of making the polymeric biguanide compositions, and the polymeric biguanides that result from those processes.

DETAILED DESCRIPTION OF THE INVENTION

Figure 1:
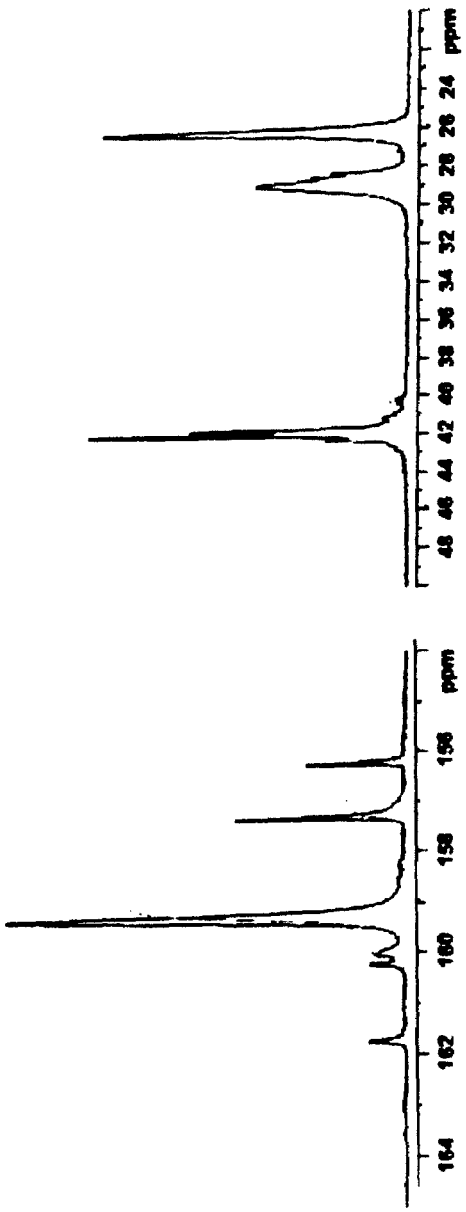
FIG. 1 is a $^{13}$C NMR spectrum of a polymeric biguanide composition of the invention.
Figure 2:
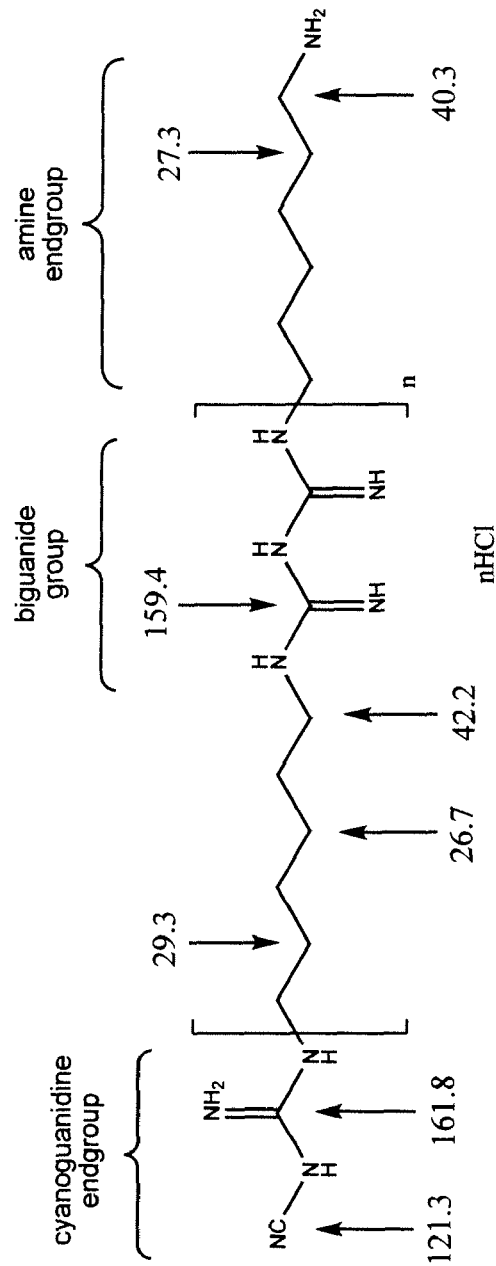
FIG. 2 shows the assigned peak assignments of a $^{13}$C NMR spectrum of a commercial sample of PHMB.
Figure 2:
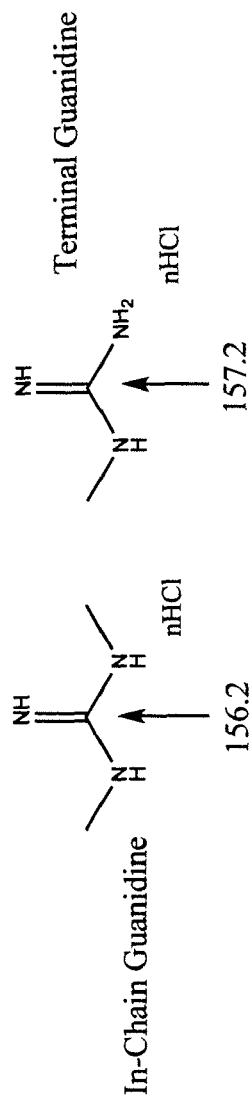

PHMB is a mixture of various biguanide polymers that can include different combinations of terminal groups, e.g., amine, cyanoguanidino, and guanidine. Based only on these three terminal groups, at least six possible biguanide polymers can exist. There can be one biguanide polymer with two terminal amine groups, which we refer to as PHMB-AA, one with two terminal cyanoguanidino groups, which we refer to as PHMB-CGCG, and one with two terminal guanidine groups, which we refer to as and PHMB-GG (see, below). There are also the three possible biguanide polymers having a combination of two different terminal groups. Again, based on the above terminal groups they include amine-cyanoguanidino (PHMB-ACG), amine-guanidino (PHMB-AG) and guanidine-cyanoguanidino (GCG). Accordingly, a commercial sample of PHMB will likely comprise a mixture of polymeric biguanides with the three mentioned terminal groups though how these terminal groups are arranged on each polymer and what the molar concentration of each type of terminal groups is in the mixture provides a relatively complex picture of the polymeric biguanide composition. Moreover, some of the composition can include in-chain polymeric guanide (not shown). The subscript "n" represents the average number of repeating groups, and a distribution of polymer length exists for each of the polymers shown below

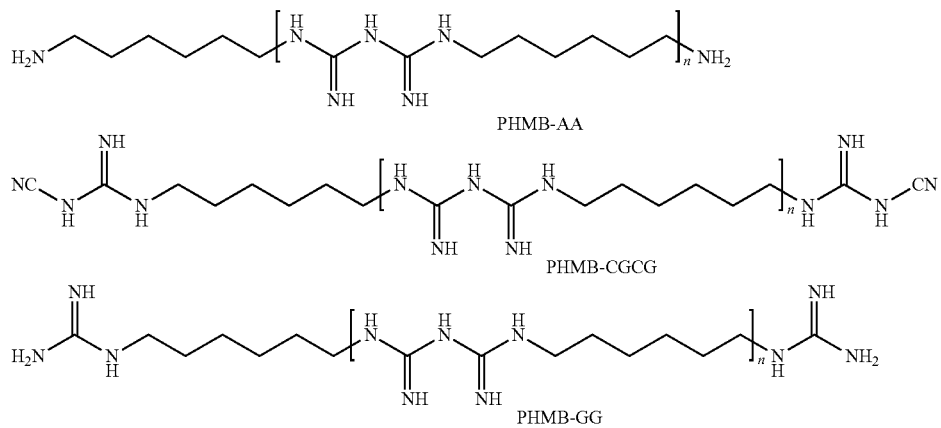

Using $^{13}$C NMR we have estimated the molar concentration of terminal amine groups in commercial PHMB (Cosmocil® type PHMB) to range from 20% to 30%. Similarly, we have estimated the molar concentration of terminal guanidine groups and terminal cyanoguanidino groups to range from 38% to 49% and 30% to 32%, respectively (see, Table 8). In contrast, the polymeric biguanide compositions of the invention are characterized by a relatively low molar concentration of terminal amine groups than the commercial samples of PHMB, that is, Cosmocil® type PHMB. The polymeric biguanide compositions are also characterized by a relatively high molar concentration of terminal guanidine groups or terminal cyanoguanidino groups than the commercial samples of PHMB.

One embodiment of the invention is directed to a polymeric biguanide composition that comprises less than 18 mol % of terminal amine groups, and 55 mol % or greater of terminal guanidine groups as measured by $^{13}$C NMR.

The term "measured by $^{13}$C NMR" means to relatively quantify specific carbon peaks associated with each type of terminal group or in-chain biguanide/guanide for a polymeric biguanide composition using the pulse technique described under the subheading Examples.

In exemplary embodiments, the polymeric biguanide composition comprises less than 15 mol %, or less than 10 mol %, of terminal amine groups, and 60 mol % or greater, or 65 mol % or greater, of terminal guanidine groups.

Alternatively, the polymeric biguanide composition comprises 55 mol % to 90 mol % terminal guanidino groups, 5 mol % to 35 mol % terminal cyanoguanidino groups and less than 18 mol % terminal amine groups. In another embodiment, the polymeric biguanide composition comprises 60 mol % to 90 mol % terminal guanidino groups, 8 mol % to 25 mol % terminal cyanoguanidino groups and less than 12 mol % terminal amine groups.

In one embodiment, the polymeric biguanide composition comprises polymeric biguanides of formula (1), formula (2), formula (3) and optionally formula (4), and has a molar ratio of

[mol % formula (1)+mol % formula (2)]|[mol % formula (3)+mol % formula (4)] from 70:30 or greater,

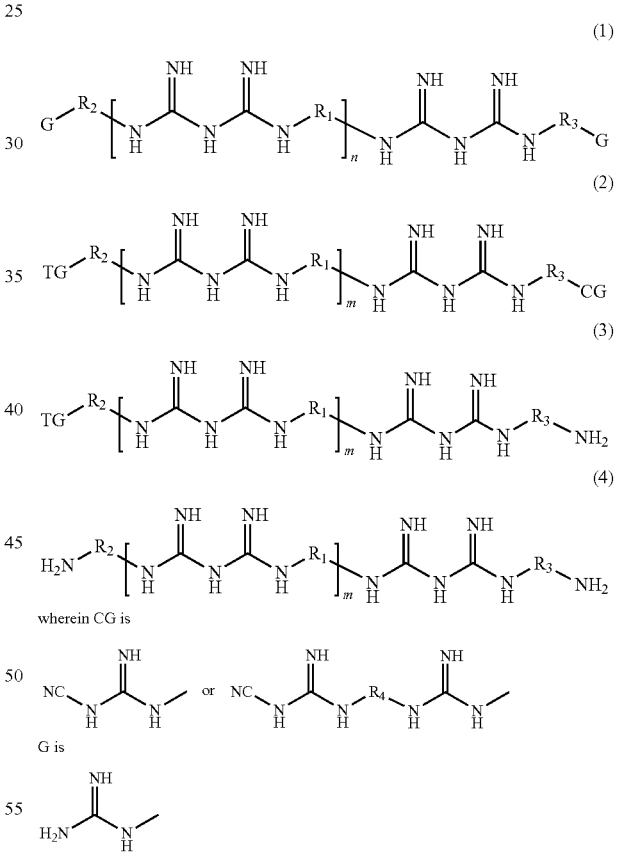

and each TG is the same or different and is selected from CG or G. $R_1$, $R_2$ and $R_3$ are divalent radicals of an aliphatic hydrocarbon independently selected from the group consisting of a $C_3$-$C_{12}$ alkylene, $C_4$-$C_{12}$ oxyalkylene and $C_4$-$C_{12}$ thioalkylene. In one embodiment, $R_1$, $R_2$ and $R_3$ are independently selected from a $C_4$-$C_8$ alkylene. $R_4$ is selected from the group consisting of a $C_2$-$C_{12}$ alkylene, $C_4$-$C_{12}$ oxyalkylene and $C_4$-$C_{12}$ thioalkylene, preferably a $C_4$-$C_{12}$ alkylene. The value n represents a number average of repeat units between 1 and 20, and the value m is independently selected for each of formulas (2), (3) and (4) and represents a number average of repeat units between 1 and 20.

It is believed that the increase in terminal guanidine groups results in part from the cleavage of the in-chain biguanide over time during preparation of the polymeric biguanide composition. This is supported in-part by the observed decrease of the in-chain biguanide content as the preparation heating time is increased from one to four hours at the same temperature.

Ordinarily, one should observe a decrease in the number average molecular weight ($M_N$) as a result of the biguanide cleavage. We observe, however, a slight increase in $M_N$, which is also dependent upon the preparation heating time (longer heating times results in higher $M_N$). These observations suggest that the preparation may also involve formation of in-chain biguanide by the reaction of a terminal amine group of one polymer with a terminal cyanoguanidino group of another polymer, and thus, resulting in a composition of slightly higher $M_N$. In combination, these two processes will tend to lower the mol % of terminal amine groups and increase the mol % of terminal guanidine groups.

In addition, as a result of the two above described processes, one would expect that on average, polymers of formula (1) will likely have a lower $M_N$, and consequently, the average value of n in formula (1) should be lower than the average value of m in formula (2) or formula (3).

In another embodiment, the polymeric biguanide composition comprises polymeric biguanides of formula (1) and formula (2)

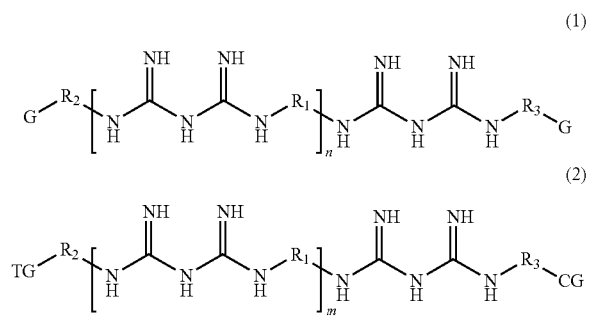

wherein the polymeric biguanides of formula (1) and formula (2) account for at least 80 mol %, or at least 90 mol %, of the total moles of polymeric biguanides in the composition, wherein

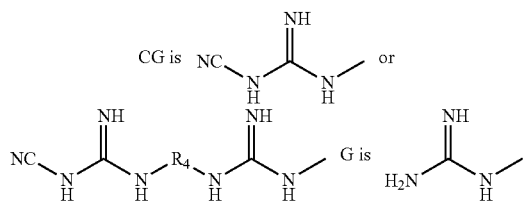

and each TG is the same or different and is selected from CG or G;

$R_1$, $R_2$ and $R_3$ are divalent radicals of an aliphatic hydrocarbon independently selected from the group consisting of a $C_3$-$C_{12}$ alkylene, $C_4$-$C_{12}$ oxyalkylene and $C_4$-$C_{12}$ thioalkylene;

$R_4$ is selected from the group consisting of a $C_2$-$C_{12}$ alkylene, $C_4$-$C_{12}$ oxyalkylene and $C_4$-$C_{12}$ thioalkylene, preferably a $C_4$-$C_{12}$ alkylene; and n and m represent a number average of repeat units between 1 and 20. Again, for the reasons described above, one can expect the average value of n in formula (1) should be lower than the average value of m in formula (2).

The invention is also directed to a polymeric biguanide composition comprising less than 18 mol % of terminal amine groups, 40 mol % or greater of terminal cyanoguanidino groups and less than 50 mol % of terminal guanidine groups, as measured by $^{13}C$ NMR. The polymeric biguanide composition also is characterized by a relative decrease in the molar concentration of terminal guanidine groups. This biguanide composition is prepared by using a similar synthetic route as that of conventional PHMB, e.g., the preparation of Cosmocil® type PHMB, with the exception that one adds from 15% to 40% by weight of a cyanoguanidino agent, e.g., hexamethylene bis(cyanoguanidino) (HMBDA), to the reaction mixture.

In exemplary embodiments, the polymeric biguanide composition comprises less than 15 mol % of terminal amine groups, and 50 mol % or greater of terminal cyanoguanidino groups. Also, the biguanide composition will comprise from 10 mol % to 30 mol % of terminal guanidine groups.

In one embodiment, the polymeric biguanide composition comprises 45 mol % to 70 mol % terminal cyanoguanidino groups, 10 mol % to 30 mol % of terminal guanidine groups and 7 mol % to 15 mol % terminal amine groups.

The polymeric biguanide composition with the relatively high terminal cyanoguanidino groups is typically characterized by in-chain biguanide concentration of 90 mol % or greater, or 92 mol % or greater, which is similar to, and typically greater than that observed in commercial PHMB (89 mol % to 92 mol %). One particular preparation provided an in-chain biguanide concentration of about 95 mol %.

Similar to the first described biguanide composition, the polymeric biguanide composition with high terminal cyanoguanidino groups can comprise polymeric biguanides of formula (1) and formula (2)

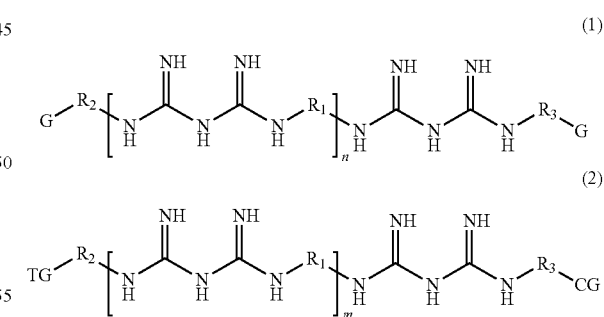

wherein the polymeric biguanides of formula (1) and formula (2) account for at least 80 mol % of the total moles of polymeric biguanides in the composition, wherein

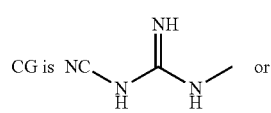

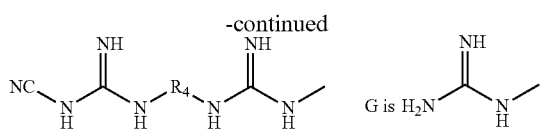

and each TG is the same or different and is selected from CG or G;

R$_1$, R$_2$ and R$_3$ are divalent radicals of an aliphatic hydrocarbon independently selected from the group consisting of a C$_3$-C$_{12}$ alkylene, C$_4$-C$_{12}$ oxyalkylene and C$_4$-C$_{12}$ thioalkylene;

R$_4$ is selected from the group consisting of a C$_2$-C$_{12}$ alkylene, C$_4$-C$_{12}$ oxyalkylene and C$_4$-C$_{12}$ thioalkylene, preferably a C$_4$-C$_{12}$ alkylene; and n and m represent a number average of repeat units between 1 and 20.

The M$_N$ of the biguanide polymers compositions of the inventions will range from 700 Da to 12,000 Da, from 1000 Da to 8,000 Da, or from 1000 Da to 4000 Da. Accordingly, the average values of m, n and p, and R$_1$, R$_2$ and R$_3$ are selected to provide biguanide polymers within this range of average number molecular weight.

Any one of the above polymeric biguanide compositions can be used as an antimicrobial component of an ophthalmic composition. For example, the polymeric biguanide compositions can be used as a component in a contact lens solution to clean, disinfect or package the lens. Alternatively, the polymeric biguanide composition can be used to preserve an ophthalmic composition or as a preservative in a pharmaceutical composition that includes a pharmaceutical agent.

As used herein, the term "ophthalmic composition" defines a composition intended for application in the eye or intended for treating a device to be placed in contact with the eye such as a contact lens. Ophthalmic compositions can include compositions for direct placement in the eye, including eye drop solutions such as for treating dry eye, and contact lens treating solutions. Ophthalmic compositions also include those compositions formulated as multi-purpose solutions for cleaning and disinfecting contact lenses or to package contact lens.

The term "preservative" or "to preserve" refers to the use of the compositions for the purpose of inhibiting the growth of microorganisms in a particular product, e.g., in an eye drop formulation.

Preparation of the Polymeric Biguanides Compositions

The polymeric biguanides can be prepared from commercially available polymeric biguanide compositions. For example, PHMB can be used as a starting material to which is added a cyanoguanidino agent, guanidine agent or a mixture thereof in the presence of a mineral acid or an organic acid. The resulting product is characterized by an increase concentration of guanidine or cyanoguanidino terminal groups at the expense of the amino terminal groups. The amount of cyanoguanidino agent or guanidine agent added will depend upon the desired degree of cyanoguanidino(guanidine)/amine exchange. Theoretically, to exchange most, if not all, of the amine terminal groups in a commercial sample of PHMB, one would add approximately four molar equivalents of cyanoguanidino agent, guanidine agent or a mixture thereof for each mole equivalent of PRMB as there are about four molar equivalents of terminal amine groups for every mole of PHMB.

In one embodiment, a reaction mixture is prepared by grinding together fine particles of a commercial sample of PHMB and a bis-cyanoguanidino alkane. The ground mixture is added to a reaction flask along with a small amount of acid, e.g., a mineral acid or an organic acid, to facilitate the exchange reaction. The reaction flask is heated to 120° C. or more, e.g., above 140° C. or 150° C., for a period of about one to about four hours. It is to be understood by one of ordinary skill, that in general, lower reaction temperatures would require longer reaction times. The reaction mixture is cooled and the resulting solids dissolved in a first solvent and then precipitated by the addition of a second solvent. For example, the first solvent can be water and the second solvent can be acetone.

Alternatively, one can use a dicyanamide such as sodium dicyanamide or zinc dicyanamide as the cyanoguanidino agent. Again, to theoretically exchange all of the amino terminal groups one would add about four molar equivalents of the dicyanamide for each molar equivalent of commercial PHMB. The PHMB and dicyanamide are added to a reaction vessel and heated. After heating at about 150° C. for about one to about four hours the reaction is cooled to room temperature under nitrogen overnight. The resulting solids are dissolved in water and reprecipitated with acetone.

Dialysis can be used as an alternative approach to remove reaction impurities and undesired, low molecular weight products and reactants from the resulting reaction solids. In this case, the reaction solids are dissolved in water and the solution undergoes dialysis (100 MWCO tubing) overnight. The resulting product is then freeze-dried.

In another embodiment, the polymeric biguanide compositions can be prepared using a modified synthetic preparation of commercial PHMB. In this case, approximately, 10 mol % to 50 mol %, or 20 mol % to 40 mol % (based on the moles of diamine), of the cyanoguanidino agent, guanidine agent or mixture thereof, is added to the reaction mixture. A preparation of PHMB is reported in U.S. Pat. No. 3,428,576 (Examples 1 to 3).

Polymeric Biguanide Compositions and the Use Thereof in Antimicrobial Formulations The polymeric biguanides of the invention can be used for skin cleansers, skin disinfectants, antibacterial soap, skin lotions, shampoo, hair conditioners, topical gels, topical ointments, topical medicaments with or without an active pharmaceutical agent, toothpaste, mouthwash, medicine that is taken orally or is intended to treat conditions in the mouth, nasal spray, optic medicament, genital cream, vaginal cream, vaginal ointment, spermicidal agents, medicament, eye drops, eye sprays, ophthalmic solutions or gels, or ophthalmic ointments.

The polymeric biguanides can be formulated as an antimicrobial component for an ophthalmic lens care solution, which can be used to clean, disinfect or package contact lenses. In this case, the polymeric biguanides will be formulated with a number of other solution components that provide additional properties required of such solutions.

The polymeric biguanides can be formulated with other cationic antimicrobial components. Suitable antimicrobial components include, but are not limited to, quaternary ammonium salts used in ophthalmic applications such as poly[dimethylimino-2-butene-1,4-diyl] chloride, α-[4-tris(2-hydroxyethyl)ammonium chloride-2-butenyl]poly[1-dimethylammonium chloride-2-butenyl]-ω-tris(2-hydroxyethyl)ammonium chloride (CAS# 68518-54-7, available as Polyquaternium-1® from Stepan Corporation), myristamidopropyl dimethylamine (Aldox®), benzalkonium halides, and biguanides such as salts of alexidine, alexidine-free base, salts of chlorhexidine, antimicrobial polypeptides and mixtures thereof.

The term "cationic" when referring to an antimicrobial component refers to the predominant form of the antimicrobial component at neutral pH having a positive charge and a counteranion. An exemplary list of cationic disinfecting antimicrobial components include poly[dimethylimino-2-butene-1,4-diyl] chloride, α-[4-tris(2-hydroxyethyl)ammonium chloride-2-butenyl]poly[1-dimethylammonium chloride-2-butenyl]-ω-tris(2-hydroxyethyl) ammonium chloride, myristamidopropyl dimethylamine, and any mixture thereof.

The cationic antimicrobial component is present in an amount from 0.01 ppm to 100 ppm, from 0.1 ppm to 50 ppm or from 0.1 ppm to 10 ppm. It is preferred, however, that the amount of antimicrobial component that is used is effective in disinfecting contact lenses contacted with the compositions, while at the same time promote lens patient comfort and acceptability. Typically, an amount of the antimicrobial component is used to reduce the microbial burden or load on the contact lens by one log order in four hours. Alternatively, an effective amount of the antimicrobial component reduces the microbial load by one log order in one hour. The reductions are based upon similarly prepared lens solutions absent the cationic antimicrobial component.

In one embodiment, the primary antimicrobial component present in the lens care solutions is one of the polymeric biguanide compositions, which is present from 0.01 ppm to 3 ppm. In another embodiment, the primary antimicrobial component present in the lens care solution is α-[4-tris(2-hydroxyethyl)ammonium chloride-2-butenyl]poly[1-dimethylammonium chloride-2-butenyl]-ω-tris(2-hydroxyethyl) ammonium chloride, which is present from 1 ppm to 100 ppm, and the polymeric biguanide of the invention is used as a secondary antimicrobial component.

In addition, any one mixture of two cationic antimicrobial components can be present in the lens care solutions. For example, a particular lens care solution can include from 0.3 ppm to 0.8 ppm of the polymeric biguanide, and 10 ppm to 60 ppm α-[4-tris(2-hydroxyethyl)ammonium chloride-2-butenyl]poly[1-dimethylammonium chloride-2-butenyl]-ω-tris (2-hydroxyethyl)ammonium chloride.

The ophthalmic lens care solutions can also include a fatty acid monoester along with one of the polymeric biguanide compositions. The fatty acid monoester comprises an aliphatic fatty acid portion having ten carbon atoms, and an aliphatic hydroxyl portion. In some instances, and depending upon the particular type of contact lens, the presence of the fatty acid monoester can enhance the efficacy against *Candida albicans* or *Fusarium solani*.

The lens care solutions can also include a phosphonic acid, or its physiologically compatible salt, that is represented by the following formula:

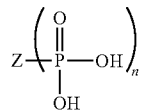

wherein Z is a connecting radical equal, n is an integer from 1 to 4, or 1, 2 or 3, and preferably containing 1 to 12 carbon atoms, more preferably 3 to 10 carbon atoms. The Z radical comprises substituted or unsubstituted saturated hydrocarbon radicals or amine-containing radicals, which amine-containing radicals are saturated hydrocarbon radicals in which the carbon atoms are interrupted with at least one nitrogen atom such as 1, 2 or 3 nitrogen atoms that forms a secondary or tertiary amine.

Accordingly, suitable Z radicals include substituted or unsubstituted alkylidene, substituted or unsubstituted alkylene, amino tri(alkylene) having at least n+1 carbon atoms, amino di(alkylene) having at least n+1 carbon atoms, alkylenediaminetetra(alkylene) or a dialkylenetriamine penta (alkylene) radical. In each case, the alkylene group in parenthesis is connected to a phosphonic acid group. Preferably, all alkylene groups independently have 1 to 4 carbon atoms.

Exemplary compounds in which the Z group is an amino tri(alkylene) radical includes amino tri(ethylidene phosphonic acid), amino tri(isopropylidene phosphonic acid), amino di(methylene phosphonic acid) mono(isopropylidene phosphonic acid), and amino mono(methylene phosphonic acid) di(ethylidene phosphonic acid). Exemplary compounds in which the Z group is a substituted or unsubstituted alkylidene radical includes methylene diphosphonic acid, ethylidine diphosphonic acid, 1-hydroxy propylidene diphosphonic acid. Exemplary compounds in which the Z group is an alkylenediaminetetra(alkylene) or a dialkylenetriamine penta (alkylene) radical include hexamethylenediaminetetra(methylene phosphonic acid) and diethylenetriaminepenta (methylenephosphonic acid).

In one embodiment, the phosphonic acid, or its physiologically compatible salt, is represented by the following formula:

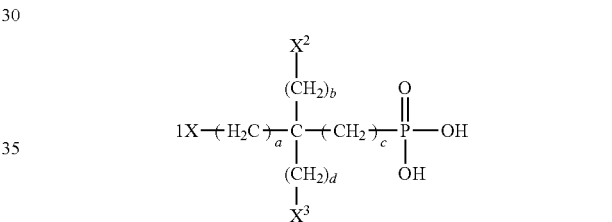

wherein each of a, b, c, and d are independently selected from integers from 0 to 4, preferably 0 or 1; $X^1$ is a phosphonic acid group (i.e., $P(OH)_2O$), hydroxy, amine or hydrogen; and $X^2$ and $X^3$ are independently selected from the group consisting of halogen, hydroxy, amine, carboxy, alkylcarbonyl, alkoxycarbonyl, or substituted or unsubstituted phenyl, and methyl. Exemplary substituents on the phenyl are halogen, hydroxy, amine, carboxy and/or alkyl groups. A particularly preferred species is that wherein a, b, c, and d in are zero, specifically the tetrasodium salt of 1-hydroxyethylidene-1,1-diphosphonic acid, also referred to as tetrasodium etidronate, commercially available from Monsanto Company as DeQuest® 2016 diphosphonic acid sodium salt or phosphonate.

The lens care solutions can also include dexpanthenol, which is an alcohol of pantothenic acid, also called Provitamin B5, D-pantothenyl alcohol or D-panthenol. In some formulations of the lens care compositions, dexpanthenol can exhibit good cleansing action and can stabilize the lachrymal film at the eye surface when placing a contact lens on the eye. Dexpanthenol is preferably present in the contact lens care compositions in an amount from 0.2% to 10% (w/v), from 0.5% to 5% (w/v), or from 1% to 3% (w/v).

The lens care solutions can also include sorbitol, which is a hexavalent sugar alcohol. Typically, dexpanthenol is used in combination with sorbitol. In specific formulations the combination dexpanthenol and sorbitol can provide enhanced cleansing action and can also stabilize the lachrymal film following placement of the contact lens on the eye. These formulations can substantially improve patient comfort when wearing contact lenses. Sorbitol is present in the lens care compositions in an amount from 0.4% to 10% (w/v), from 0.8% to 6% (w/v) or from 1% to 3% (w/v).

The lens care solutions can also include one or more neutral or basic amino acids. The neutral amino acids include: the alkyl-group-containing amino acids such as alanine, isoleucine, valine, leucine and proline; hydroxyl-group-containing amino acids such as serine, threonine and 4-hydroxyproline; thio-group-containing amino acids such as cysteine, methionine and asparagine. Examples of the basic amino acid include lysine, histidine and arginine. The one or more neutral or basic amino acids are present in the compositions at a total concentration of from 0.1% to 5% (w/v).

The lens care solutions can also include glycolic acid, asparatic acid or any mixture of the two at a total concentration of from 0.001% to 4% (w/v) or from 0.01% to 2.0% (w/v).

In addition, the combined use of one or more amino acids and glycolic acid and/or asparatic acid can lead to a reduction in the change of the size of the contact lens due to swelling and shrinkage following placement of the lens on the eye. The stated combination provides a higher degree of compatibility with the contact lens compared to the absence of one of the two components in the composition. It is believed that one or more of the amino acids can cause the lens to swell, and that the glycolic acid and/or asparatic acid can cause the contact lens to shrink. If used in combination, however, a mutual counteraction of the two observed affects is believed to exist.

The lens care solutions can also include glycolic acid, asparatic acid or any mixture of the two, in combination with 2-amino-2-methyl-1,3-propanediol or a salt thereof. In some cases, solutions that contain a mixture of two of the three, or all three, compounds minimize the change of the lens size following placement of the contact lens in the eye. The 2-amino-2-methyl-1,3-propanediol (AMPD) or the salt thereof is added to the solutions in an amount to satisfy a predetermined molar ratio of glycolic acid, asparatic acid or any mixture of the two and AMPD. The molar ratio of the two components glycolic acid and/or asparatic acid to AMPD is 1:20 to 1.3:1. The glycolic acid, asparatic acid or any mixture of the two is present in the compositions at a concentration of 0.01% to 5% (w/v) or at a concentration of 0.05% to 1% (w/v).

If the components glycolic acid and/or asparatic acid, and AMPD, are present in the compositions in the absence of the other, one may observe a tendency to cause shrinkage or swelling of the lens. However, if these two components are combined together and used in the predetermined molar ratio, little, if any, change in the size of the lens is observed.

The amount of AMPD present in the solutions can be determined according to the amount of glycolic acid and/or asparatic acid in the composition. As stated, AMPD is present in an amount to provide a molar ratio of glycolic acid and/or asparatic acid to AMPD to be from 1:20 to 1.3:1, from 1:15 to 1.2:1 or from 1:14 to 1:1. If the amount of AMPD exceeds 20 mols per 1 mol of glycolic acid and/or asparatic, adsorption of the cationic antimicrobial component on the contact lens will occur. If the amount of AMPD is less than 1 mol per 1.3 mols of glycolic acid and/or asparatic acid, a reduction in antimicrobial efficacy of the composition is observed.

The contact lens care solutions will very likely include a buffer system. By the terms "buffer" or "buffer system" is meant a compound that, usually in combination with at least one other compound, provides a buffering system in solution that exhibits buffering capacity, that is, the capacity to neutralize, within limits, either acids or bases (alkali) with relatively little or no change in the original pH. Generally, the buffering components are present from 0.05% to 2.5% (w/v) or from 0.1% to 1.5% (w/v).

The term "buffering capacity" is defined to mean the millimoles (mM) of strong acid or base (or respectively, hydrogen or hydroxide ions) required to change the pH by one unit when added to one liter (a standard unit) of the buffer solution. The buffer capacity will depend on the type and concentration of the buffer components. The buffer capacity is measured from a starting pH of 6 to 8, preferably from 7.4 to 8.4.

Borate buffers include, for example, boric acid and its salts, for example, sodium borate or potassium borate. Borate buffers also include compounds such as potassium tetraborate or potassium metaborate that produce borate acid or its salt in solutions. Borate buffers are known for enhancing the efficacy of certain polymeric biguanides. For example, U.S. Pat. No. 4,758,595 to Ogunbiyi et al. describes that a contact-lens solution containing a polyaminopropyl biguanide (PAPB), also known as PHMB, can exhibit enhanced efficacy if combined with a borate buffer.

A phosphate buffer system preferably includes one or more monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$) and potassium monobasic phosphate ($KH_2PO_4$). The phosphate buffer components frequently are used in amounts from 0.01% or to 0.5% (w/v), calculated as phosphate ion.

Other known buffer compounds can optionally be added to the lens care compositions, for example, citrates, citric acid, sodium bicarbonate, TRIS, and the like. Other ingredients in the solution, while having other functions, may also affect the buffer capacity. For example, EDTA, often used as a complexing agent, can have a noticeable effect on the buffer capacity of a solution.

A preferred buffer system is based upon boric acid/borate, a mono and/or dibasic phosphate salt/phosphoric acid or a combined boric/phosphate buffer system. For example a combined boric/phosphate buffer system can be formulated from a mixture of sodium borate and phosphoric acid, or the combination of sodium borate and the monobasic phosphate.

In a combined boric/phosphate buffer system, the solution comprises about 0.05 to 2.5% (w/v) of a phosphoric acid or its salt and 0.1 to 5.0% (w/v) of boric acid or its salt. The phosphate buffer is used (in total) at a concentration of 0.004 to 0.2 M (Molar), preferably 0.04 to 0.1 M. The borate buffer (in total) is used at a concentration of 0.02 to 0.8 M, preferably 0.07 to 0.2 M.

The lens care solutions can also include a water-soluble borate-polyol complex which can be formed by mixing a source of borate with a polyol of choice in an aqueous solution. These complexes can be used in conjunction with the cationic antimicrobial component above, and can help to meet preservative efficacy and disinfection standards. In such compositions, the molar ratio of borate to polyol is generally from 1:0.1 to 1:10, or from 1:0.25 to 1:2.5. If present in the lens care solutions, the borate-polyol complex is usually present from 0.5% to 5% (w/v), from 1.0% to 2.5% (w/v). The borate-polyol complexes are described in greater detail in U.S. Pat. No. 6,143,799.

The lens care solutions will very likely comprise effective amounts of one or more known lens care formulation components such as a detergent or surfactant component, a viscosity inducing or thickening component, a chelating or sequestering component, or a tonicity component. The additional component or components can be selected from materials which are known to be useful in contact lens care solutions and are included in amounts effective to provide the desired effect or benefit.

Suitable surfactants can be either amphoteric, cationic, anionic, or nonionic, and are typically present (individually or in combination) in amounts up to 15%, or up to 5% (w/v). One preferred surfactant class are the amphoteric or nonionic surfactants. The surfactant should be soluble in the lens care solution and non-irritating to eye tissues. Many nonionic surfactants comprise one or more chains or polymeric components having oxyalkylene (—O—R—) repeats units wherein R has 2 to 6 carbon atoms. Preferred non-ionic surfactants comprise block polymers of two or more different kinds of oxyalkylene repeat units, which ratio of different repeat units determines the HLB of the surfactant. Satisfactory non-ionic surfactants include polyethylene glycol esters of fatty acids, e.g. coconut, polysorbate, polyoxyethylene or polyoxypropylene ethers of higher alkanes ($C_{12}$-$C_{18}$). Examples of the this class include polysorbate 20 (available under the trademark Tween® 20), polyoxyethylene (23) lauryl ether (Brij® 35), polyoxyethyene (40) stearate (Myrj®52), polyoxyethylene (25) propylene glycol stearate (Atlas® G 2612). Still other preferred surfactants include tyloxapol, betaine-type surfactants, polysulfates, polyethylene glycol, alkyl esters and any mixture thereof.

A particular non-ionic surfactant consisting of a poly(oxypropylene)-poly(oxyethylene) adduct of ethylene diamine having a molecular weight from about 7,500 to about 27,000 wherein at least 40 weight percent of said adduct is poly(oxyethylene) has been found to be particularly advantageous for use in cleaning and conditioning both soft and hard contact lenses when used in amounts from about 0.01 to about 15 weight percent. The CTFA Cosmetic Ingredient Dictionary's adopted name for this group of surfactants is poloxamine. Such surfactants are available from BASF Wyandotte Corp., Wyandotte, Mich., under Tetronic®.

An analogous of series of surfactants, for use in the lens care compositions, is the poloxamer series which is a poly(oxyethylene) poly(oxypropylene) block polymers available under Pluronic® (commercially available form BASF). In accordance with one embodiment of a lens care composition the poly(oxyethylene)-poly(oxypropylene) block copolymers will have molecular weights from 2500 to 13,000 daltons or from 6000 to about 12,000 daltons. Specific examples of surfactants which are satisfactory include: poloxamer 108, poloxamer 188, poloxamer 237, poloxamer 238, poloxamer 288 and poloxamer 407. Particularly good results are obtained with poloxamer 237.

Various other ionic as well as amphoteric and anionic surfactants suitable for in the invention can be readily ascertained, in view of the foregoing description, from McCutcheon's Detergents and Emulsifiers, North American Edition, McCutcheon Division, MC Publishing Co., Glen Rock, N.J. 07452 and the CTFA International Cosmetic Ingredient Handbook, Published by The Cosmetic, Toiletry, and Fragrance Association, Washington, D.C.

Amphoteric surfactants suitable for use in a composition according to the present invention include materials of the type are offered commercially under the trade name "Miranol." Another useful class of amphoteric surfactants is exemplified by cocoamidopropyl betaine, commercially available from various sources.

The foregoing surfactants will generally be present in a total amount from 0.01% to 5% (w/v), from 0.1% to 5% (w/v), or from 0.1% to 1.5% (w/v). Often the amount of surfactant is from 0.005% or 0.01%, to 0.1% or 0.5% or 0.8% (w/v).

The lens care solutions can also include a viscosity enhancing component. The viscosity inducing components should be compatible with the other components and are preferably nonionic. Such viscosity inducing components are effective to enhance and/or prolong the cleaning and wetting activity of the surfactant component and/or condition the lens surface rendering it more hydrophilic (less lipophilic) and/or to act as a demulcent on the eye. Increasing the solution viscosity provides a film on the lens which may facilitate comfortable wearing of the contact lens. The viscosity inducing component can also function to cushion the impact on the eye surface during placement of the lens and serves also to alleviate eye irritation.

Suitable viscosity inducing components include, but are not limited to, water soluble natural gums, cellulose-derived polymers and the like. Useful natural gums include guar gum, gum tragacanth and the like. Useful cellulose-derived viscosity inducing components include cellulose-derived polymers, such as hydroxypropyl cellulose, hydroxypropylmethyl cellulose, carboxymethyl cellulose, methyl cellulose, hydroxyethyl cellulose and the like. A very useful viscosity inducing component is hydroxypropylmethyl cellulose (HPMC). Another useful viscosity inducing component is a polymer comprising monomeric units of 2-methacryloyloxy ethyl phosphorylcholine (MPC), which is available under the tradename Lipidure® from NOF Corporation.

The viscosity inducing component is used in an amount effective to increase the viscosity of the solution, preferably to a viscosity in the range of about 1.5 to about 30, or even as high as about 750, cps at 25° C., as determined by USP test method No. 911 (USP 23, 1995).

A chelating or sequestering can be included in an amount effective to enhance the effectiveness of the cationic antimicrobial component and/or to complex with metal ions to provide more effective cleaning of the contact lens. A wide range of organic acids, amines or compounds which include an acid group and an amine function are capable of acting as chelating components. For example, nitrilotriacetic acid, diethylenetriaminepentacetic acid, hydroxyethylethylene-diaminetriacetic acid, 1,2-diaminocyclohexane tetraacetic acid, hydroxyethylaminodiacetic acid, ethylenediamine-tetraacetic acid and its salts, polyphosphates, citric acid and its salts, tartaric acid and its salts, and the like and mixtures thereof, are useful as chelating components. Ethylenediaminetetraacetic acid (EDTA) and its alkali metal salts, are preferred, with disodium salt of EDTA, also known as disodium edetate, being one of the preferred chelating components.

The lens care solutions will typically have an osmolality in the range of at least about 200 mOsmol/kg for example, about 300 or about 350 to about 400 mOsmol/kg. The lens care solutions are substantially isotonic or hypertonic (for example, slightly hypertonic) and are ophthalmically acceptable.

The lens care solutions will typically include an effective amount of a tonicity adjusting component. Among the suitable tonicity adjusting components that can be used are those conventionally used in contact lens care products such as various inorganic salts. Sodium chloride and/or potassium chloride and the like are very useful tonicity components. The amount of tonicity adjusting component is effective to provide the desired degree of tonicity to the solution.

Accordingly, the polymeric biguanide compositions can be used as a primary or a secondary antimicrobial component in a disinfecting/cleaning contact lens solution. In general, such a method would include contacting or soaking the lenses with the solution for a period of time, typically for a minimum of one to four hours. Although such contacting may be accomplished by simply soaking a lens in the ophthalmic composition, greater preserving, disinfecting and/or cleaning may possibly be achieved if a few drops of the solution are initially placed on each side of the lens, and the lens is rubbed for a period of time, for example, approximately 20 seconds. The lens can then be subsequently immersed within several milliliters of the solution. Preferably, the lens is permitted to soak in the solution for at least four hours. Furthermore, the lens is preferably rinsed with fresh composition after any rubbing step and again after being immersed within the solution. The lenses are removed from the solution, rinsed with the same or a different solution, for example, a preserved isotonic saline solution, and repositioned on the eye.

The formulated contact lens solutions containing the polymeric biguanides can be used with many different types of contact lenses including: (1) hard lenses formed from materials prepared by polymerization of acrylic esters, such as poly(methyl methacrylate) (PMMA), (2) rigid gas permeable (RGP) lenses formed from silicone acrylates and fluorosilicone methacrylates, (3) soft, hydrogel lenses, and (4) non-hydrogel elastomer lenses.

As an example, soft hydrogel contact lenses are made of a hydrogel polymeric material, a hydrogel being defined as a crosslinked polymeric system containing water in an equilibrium state. In general, hydrogels exhibit excellent biocompatibility properties, i.e., the property of being biologically or biochemically compatible by not producing a toxic, injurious or immunological response in a living tissue. Representative conventional hydrogel contact lens materials are made by polymerizing a monomer mixture comprising at least one hydrophilic monomer, such as (meth)acrylic acid, 2-hydroxyethyl methacrylate (HEMA), glyceryl methacrylate, N,N-dimethacrylamide, and N-vinylpyrrolidone (NVP). In the case of silicone hydrogels, the monomer mixture from which the copolymer is prepared further includes a silicone-containing monomer, in addition to the hydrophilic monomer. Generally, the monomer mixture will also include a crosslink monomer such as ethylene glycol dimethacrylate, tetraethylene glycol dimethacrylate, and methacryloxyethyl vinylcarbonate. Alternatively, either the silicone-containing monomer or the hydrophilic monomer may function as a crosslink agent.

The polymeric biguanide compositions can also be formulated for use as a preservative solution or packaging solution for contact lenses. One of ordinary skill in the art would know how to adjust the formulation for each of these respective applications. The lens care compositions in combination with its container or bottle and packaging, including instructions for use in accordance with a specified regimen, provides an improved kit, package, or system for the care of contact lenses.

One exemplary ophthalmic composition is formulated as a contact lens disinfecting solution prepared with the components and amounts of each listed in Table 1.

TABLE 1

| Component | Minimum Amount (wt. %) | Maximum Amount (wt. %) | Preferred Amount (wt. %) |
|---|---|---|---|
| boric acid | 0.10 | 1.0 | 0.64 |
| sodium borate | 0.01 | 0.20 | 0.09 |
| sodium chloride | 0.20 | 0.80 | 0.49 |
| EDTA | 0.01 | 0.20 | 0.11 |
| Dequest ® | 0 | 0.10 | 0.03 |
| Tetronic ® 1107 | 0.05 | 2.0 | 1.00 |
| Example 5 | 0.1 | 2 ppm | 1 ppm |

Another disinfecting solution according to the present invention includes the following ingredients listed in Table 2A.

TABLE 2A

| Component | Minimum Amount (wt. %) | Maximum Amount (wt. %) | Preferred Amount (wt. %) |
|---|---|---|---|
| sodium citrate | 0.1 | 0.8 | 0.65 |
| Tetronic ® 1304 | 0.1 | 1.0 | 0.05 |
| AMPD | 0.1 | 0.6 | 0.45 |
| sodium chloride | 0.05 | 0.8 | 0.10 |
| boric acid | 0.1 | 1.0 | 0.60 |
| disodium EDTA | 0.01 | 0.20 | 0.05 |
| sorbitol | 0.5 | 2.0 | 1.20 |
| Example 5 | 0.1 | 2 ppm | 1 ppm |
| myristamidopropyldimethylamine | 0.0001 | 0.0010 | 0.0005 |

Another disinfecting solution according to the present invention includes the following ingredients listed in Table 2B.

TABLE 2B

| Component | Minimum Amount (wt. %) | Maximum Amount (wt. %) | Preferred Amount (wt. %) |
|---|---|---|---|
| sodium citrate | 0.1 | 0.8 | 0.6 |
| sodium chloride | 0.05 | 0.8 | 0.1 |
| sodium borate | 0.10 | 1.0 | 0.60 |
| propylene glycol | 0.2 | 2.0 | 1.00 |
| Tetronic ® 1304 | 0.05 | 0.5 | 0.10 |
| nonanoyl EDTA | 0.05 | 0.5 | 0.20 |
| Example 5 | 0.1 | 2 ppm | 1 ppm |
| myristamidopropyldimethylamine | 0.0001 | 0.0010 | 0.0005 |

Another disinfecting solution according to the present invention includes the following ingredients listed in Table 3.

TABLE 3

| Component | Minimum Amount (wt. %) | Maximum Amount (wt. %) | Preferred Amount (wt. %) |
|---|---|---|---|
| sorbitol | 0.2 | 2.5 | 1.88 |
| tromethamine | 0.05 | 1.0 | 0.33 |
| Pluronic ® F127 | 0.05 | 1.0 | 0.10 |
| sodium phosphate, dihydrogen | 0.10 | 0.8 | 0.46 |
| dexpanthenol | 0.5 | 2.50 | 2.00 |
| EDTA | 0.01 | 0.20 | 0.025 |
| Example 5 | 0.5 ppm | 2 ppm | 1 ppm |

Another disinfecting solution according to the present invention includes the following ingredients listed in Table 4.

TABLE 4

| Component | Minimum Amount (wt. %) | Maximum Amount (wt. %) | Preferred Amount (wt. %) |
|---|---|---|---|
| sodium/potassium chloride | 0.2 | 2.5 | 0.70 |
| propylene glycol | 0.1 | 1.0 | 0.50 |
| poloxamer 237 | 0.01 | 0.20 | 0.05 |
| phosphate monobasic | 0.05 | 0.40 | 0.10 |
| phosphate dibasic | 0.05 | 0.4 | 0.12 |
| taurine | 0.01 | 0.10 | 0.05 |
| HPMC | 0.05 | 0.4 | 0.15 |
| EDTA | 0.006 | 0.10 | 0.01 |
| Example 5 | 0.5 ppm | 2 ppm | 1.1 ppm |

The polymeric biguanides can also be formulated as a contact lens rewetting eye drop solution. By way of example, the rewetting drops may be formulated according to any one of the foregoing formulations of Tables 1 to 4 above. Alternatively, the formulations may be modified by increasing the amount of surfactant; by reducing the amount of antimicrobial agent to a preservative amount and/or by adding a humectant and/or demulcent.

The polymeric biguanide compositions can be used as a preservative in ophthalmic compositions formulated for treating patients with dry eye. In such a method, the ophthalmic composition is administered to the patient's eye, eye lid or to the skin surrounding the patient's eye. The compositions can be administered to the eyes irrespective of whether contact lenses are present in the eyes of the patient. For example, many people suffer from temporary or chronic eye conditions in which the eye's tear system fails to provide adequate tear volume or tear film stability necessary to remove irritating environmental contaminants such as dust, pollen, or the like.

The polymeric biguanides can also be used as a preservative in pharmaceutical compositions such as nasal sprays, ear and eye drops, suppositories, and prescription and over-the-counter formulations containing a pharmaceutical active that are used or administered over time such as a cream, ointment, gel or solution.

For example, the polymeric biguanides can be used as a preservative in ophthalmic compositions for treating an ocular disease or ocular condition. In many instances, the ophthalmic compositions will include one or more active pharmaceutical agents. Generally, the active pharmaceutical agent is in one or more classes of ocular pharmaceuticals including, but not limited to anti-inflammatory agents, antibiotics, immunosuppressive agents, antiviral agents, antifungal agents, anesthetics and pain killers, anticancer agents, anti-glaucoma agents, peptide and proteins, anti-allergy agents.

In one embodiment, the active pharmaceutical agent is an anti-inflammatory agent such as a glucocorticosteroid including, but not limited to, alclometasone, algestone, amcinonide, beclomethasone, flucloronide, hydrocortisone, loteprednol etabonate, difluprednate, cortisone and combinations thereof, or a non-steroidal anti-inflammatory agent including, but not limited to, enfenamic acid, aceclofenac, bumadizon, clidanac, alminoprofen, pyrazolones, salicyclic acid, fepradinol, ampiroxicam, and combinations thereof.

In another embodiment, the active pharmaceutical agent is an antibiotic including, but not limited to, doxorubicin, apramycin, biapenem, cefaclor, ceftezole, amdinocillin, clindamycin, carbomycin, clomocycline, cinoxacin, ciprofloxacin, sulfadiazine, and combinations thereof.

In still another embodiment, the active pharmaceutical agent is an immunosuppressive agent including, but not limited to, cyclosporin A, gusperimus, fluocinolone, triaminolone, carmofur, azathioprine and combinations thereof.

In still another embodiment, the active pharmaceutical agent is an antiviral agent including, but not limited to, trisodium phosphomonoformate, trifluorothymidine, acyclovir, ganciclovir, and combinations thereof.

In still another embodiment, the active pharmaceutical agent is an antifungal agent including, but not limited to, amphotericin, neomycin, bifonazole, lanoconazole, chlorphenesin, zinc propionate and siccanin.

In still another embodiment, the active pharmaceutical agent is an antiglaucoma agent including, but not limited to, timolol, betaxolol, atenalol, acetylcholine chloride, carbachol, pilocarpine hydrochloride, and combinations thereof.

In still another embodiment, the active pharmaceutical agent is an anti-allergy agent including, but not limited to, phenylephrine hydrochloride, naphazoline hydrochloride, tetrahydrozoline hydrochloride, oxymetazoline hydrochloride, sodium cromoglycate and epinephrine.

EXAMPLES

Hexamethylene bis(cyanoguanidine) (HNMBDA) is prepared according to the method described in U.S. Pat. No. 5,965,088 (Example 1).

Comparative Example 1

An amine derivative of PHMB (PHMB-A) is prepared from commercial PHMB and hexamethylene diamine. PHMB (Cosmocil CG®, 6.0 g, 3.3 mmol), and hexamethylene diamine (0.42 g, 3.6 mmol) and concentrated hydrochloric acid (360 µL) are added to a reaction flask and heated to 100° C. until most of the liquid dissipates from the flask. The temperature of the reaction mixture is then heated to 155° C. for four hours. The reaction is allowed to cool overnight to room temperature over a flow of nitrogen. The resulting solids are dissolved in 50 mL of distilled water and solution purified by dialysis (100 MWCO tubing) overnight. The purified product is freeze dried, 4.81 g.

Example 1

Multipurpose Solution Formulations

Three multipurpose solutions were formulated with the components and amounts listed in Table 5. The formulations were labeled Formulation 1, Formulation 2 and Formulation 3, respectively.

TABLE 5

| Component | Formulation 1 (wt %) | Formulation 2 (wt %) | Formulation 3 (wt %) |
|---|---|---|---|
| boric acid | 0.64 | 0.64 | 0.64 |
| sodium borate | 0.09 | 0.09 | 0.09 |
| sodium chloride | 0.49 | 0.49 | 0.49 |
| EDTA | 0.11 | 0.11 | 0.11 |
| HAP | 0.03 | 0.03 | 0.03 |
| Tetronic ® 1107 | 1.00 | 1.00 | 1.00 |
| Example 5 | | | 1 ppm |
| PHMB-A | | 1 ppm | |
| PHMB-Cosmocil[1] | 1 ppm | | |
| Purified water | qs to 100% | qs to 100% | qs to 100% |

[1]Poly(hexamethylene biguanide) sold under the trademark Cosmocil CQ by Arch Chemical, Inc., Norwalk, Connecticut.

Example 2

Phosphate Buffered Saline PHMB Solutions

Three solutions containing three types of PHMB, i.e., PHMB Cosmocil®, PHMB-A and Example 5, were formulated in isotonic phosphate buffered saline solution as set forth in Table 6. The formulations were labeled Formulation 4, Formulation 5 and Formulation 6, respectively.

TABLE 6

| Component | Formulation 4 (wt. %) | Formulation 5 (wt. %) | Formulation 6 (wt. %) |
|---|---|---|---|
| Example 5 | | | 1 ppm |
| PHMB-Cosmocil[1] | 1 ppm | | |
| PHMB-A | | 1 ppm | |
| Phosphate buffered saline | qs to 100% | qs to 100% | qs to 100% |

[1]Poly(hexamethylene biguanide) sold under the trademark Cosmocil CQ by Arch Chemical, Inc., Norwalk, Connecticut.

Example 3

Biocidal Efficacy with Organic Soil

The microbiocidal efficacy of Formulations 1 to 6 were evaluated based upon the performance requirement referred to as the "Stand-Alone Procedure for Disinfecting Products" as outlined by the U.S. Food and Drug Administration, Division of Ophthalmic Devices. The microorganisms challenged in this procedure include: *Pseudomonas aeruginosa* (ATCC 9027), *Staphylococcus aureus* (ATCC 6538), *Serratia marcescens* (ATCC 13880), *Candida albicans* (ATCC 10231) and *Fusarium solani* (ATCC 36031). The log reduction of microorganisms determined from this testing for each formulation are shown in Table 7. No statistically significant difference was observed in the biocidal efficacy of Formulations 1 to 6.

Example 4

Comfort Related Testing

Twenty-four (24) subjects completed a two-hour, non-dispensing evaluation comparing contact lens care multipurpose solution of Formulation 1 and Formulation 3. PureVision contact lenses were used in this experiment.

Each well of the lens cases was pre-treated (a single, 4-hour minimum soak) with Formulation 1 or Formulation 3. For each case, the well to be treated with Formulation 3 was randomly determined and the fellow well received Formulation 1. All Bausch & Lomb PureVision lenses were soaked for a minimum of 4-hours with either Formulation 1 or Formulation 3, in the pre-treated lens cases, following the same randomization used for the lens case wells.

Prior to lens insertion, each patient was evaluated for comfort, corneal staining and conjunctival staining. Each subject was fitted with a pre-treated lens pair. The lens remained in the eye for two hours.

There was a statistically significant difference for mean analog comfort with respect to the Formulations (ANOVA, $p<0.03$). Formulation 3 test solution lenses received better comfort ratings than Formulation 1. The average comfort rating for Formulation 3 was 92.9; the average for Formulation 1 was 90.9 with a maximum of 100. The higher value represents a better comfort rating.

TABLE 7

Biocidal Efficacy with Organic Soil

| Formulation | Time | Log Reduction | | | | |
|---|---|---|---|---|---|---|
| | | Sa | Pa | Sm | Ca | FS |
| 1 | 30 min | 3.0 | >4.8 | 3.7 | 2.2 | 3.2 |
| | 1 hr | >5.0 | >4.8 | >5.0 | 3.0 | 4.1 |
| | 4 hr | >5.0 | >4.8 | 5.0 | 3.7 | >4.6 |
| 2 | 30 min | 2.6 | >4.8 | 3.7 | 1.9 | 3.1 |
| | 1 hr | >5.0 | >4.8 | >5.0 | 2.5 | 4.2 |
| | 4 hr | >5.0 | >4.8 | >5.0 | 3.1 | >4.6 |
| 3 | 30 min | 3.6 | >4.8 | 3.1 | 2.6 | 2.5 |
| | 1 hr | >5.0 | >4.8 | 4.4 | 3.3 | 3.5 |
| | 4 hr | >5.0 | >4.8 | >5.0 | 4.2 | 4.4 |
| 4 | 30 min | 2.8 | 3.1 | 1.8 | 0.2 | TNTC |
| | 1 hr | 3.7 | 3.7 | 2.7 | TNTC | TNTC |
| | 4 hr | 4.1 | >4.8 | 3.4 | TNTC | TNTC |
| 5 | 30 min | 2.7 | 2.9 | 1.7 | 0.3 | TNTC |
| | 1 hr | 3.3 | 3.7 | 2.7 | TNTC | TNTC |
| | 4 hr | 4.0 | >4.8 | 3.2 | TNTC | TNTC |
| 6 | 30 min | 2.9 | 3.1 | 1.7 | 0.2 | TNTC |
| | 1 hr | 3.5 | 3.9 | 2.8 | TNTC | TNTC |
| | 4 hr | 4.2 | >4.8 | 3.5 | TNTC | 2.0 |

There was a marginally statistically significant difference for mean analog sting/burn with respect to the two Formulations (ANOVA, $p=0.06$). Formulation 3 treated lenses received better sting/burn ratings than Formulation 1 treated lenses. Formulation 3 had an average sting burn rating of 95.3; Formulation 1 had a rating of 93.0. The higher value represents less stinging/burning.

There was also a statistically significant difference for mean normalized corneal staining extent between Formulation 1 and Formulation 3 at 2 hours (Wilcoxon Matched Pairs Test, $p<0.01$). There was no statistically significant difference for mean normalized corneal staining severity at 2 Hours (Wilcoxon Matched Pairs Test, $p>0.11$). Formulation 3 treated eyes exhibited less normalized corneal staining extent at 2 Hours than the Formulation 1 treated eyes. Formulation 3 had an average staining extent value of 1.5; Formulation 3 had an average staining extent value of 2.9.

There was no statistically significant difference for mean normalized conjunctival staining severity between Formulation 1 and Formulation 3 at 2 Hours (Wilcoxon Matched Pairs Test, $p>0.78$). There was no statistically significant difference for mean normalized conjunctival staining extent at 2 Hours (Wilcoxon Matched Pairs Test, $p>0.11$).

Formulation 3 soaked lenses elicited statistically significant better comfort scores and less normalized corneal staining extent at 2 hours than Formulation 1 soaked lenses. In addition, Formulation 3 soaked lenses elicited better sting/burn scores than Formulation 1 soaked lenses.

Example 5

PHMB (Cosmocil CG®, 6.0 g, 3.3 mmol), hexamethylene bis(cyanoguanido) (HMBDA) (0.9 g, 3.6 mmol) and concentrated hydrochloric acid (360 µL) are added to a reaction flask and heated to 100° C. until most of the liquid dissipates from the flask. The temperature of the reaction mixture is then heated to 155° C. for four hours. The reaction is allowed to cool overnight to room temperature over a flow of nitrogen. The resulting solids are dissolved in 50 mL of distilled water and solution purified by dialysis (100 MWCO tubing) overnight. The purified product is freeze dried, 4.81 g.

Example 6

PHMB (Cosmocil®CQ, 6.0 g, 3.3 mmol), hexamethylene bis(cyanoguanido) (HMBDA) (1.8 g, 7.2 mmol) and concentrated hydrochloric acid (720 µL) are added to a reaction flask and heated to 100° C. until most of the liquid dissipates from the flask. The temperature of the reaction mixture is then heated to 155° C. for four hours. The reaction is allowed to cool overnight to room temperature over a flow of nitrogen. The resulting solids are dissolved in 60 mL of distilled water and solution purified by dialysis (100 MWCO tubing) overnight. The purified product is freeze dried, 5.3 g.

The product was analyzed by $^{13}C$ NMR (see, below) to determine the molar concentration of terminal end groups. The $^{13}C$ NMR data for Examples 5 and 6 along with commercial samples of PHMB are summarized in Table 8.

TABLE 8

| Example | $M_n$ (GPC) | $M_n$ (NMR) | terminal groups (mol %) | | | in-chain (mol %) | |
|---|---|---|---|---|---|---|---|
| | | | amine | CG | G | GG | G |
| Cosmocil ® CQ | 1568 | 1419 | 30.2 | 31.7 | 38.0 | 91.7 | 8.3 |
| Cosmocil ® 100 | 1695 | 1383 | 20.8 | 29.9 | 49.3 | 89.6 | 10.4 |
| 5 | 1392 | 1276 | 8.4 | 25.9 | 65.7 | 89.4 | 10.6 |
| 6 | 1089 | 829 | 0 | 11.7 | 88.3 | 84.3 | 15.7 |

Examples 7A to 7C

For each of the preparations, PHMB (Cosmocil®100, 6.0 g, 3.3 mmol) (Cosmocil®100 is a solid form of PHMB), hexamethylene bis(cyanoguanido) (HMBDA) (1.8 g, 7.2 mmol) and concentrated hydrochloric acid (720 µL) are added to a reaction flask and heated to 100° C. until most of the liquid dissipates from the flask. The temperature of the reaction mixture is then heated to 155° C. for four hours. The reaction is allowed to cool overnight to room temperature over a flow of nitrogen. The resulting solids are dissolved in 60 mL of distilled water and solution purified by dialysis (100 MWCO tubing) overnight. The purified product is then freeze dried overnight.

The $^{13}C$ NMR data for Examples 7A to 7C are summarized in Table 9.

TABLE 9

| Example | $M_n$ (GPC) | $M_n$ (NMR) | terminal groups (mol %) | | | in-chain (mol %) | |
|---|---|---|---|---|---|---|---|
| | | | amine | CG | G | GG | G |
| 7A | 1808 | 1466 | 9.5 | 20.0 | 70.5 | 86.9 | 13.1 |
| 7B | 1758 | 1460 | 7.5 | 23.0 | 69.5 | 87.9 | 12.1 |
| 7C | 1751 | 1449 | 11.5 | 20.0 | 68.5 | 87.2 | 12.8 |

Examples 8A to 8D

For each of the preparations, PHMB (Cosmocil®100, 6.0 g, 3.3 mmol) (Cosmocil® 100 is a solid form of PHMB), hexamethylene bis(cyanoguanido) (HMBDA) (1.8 g, 7.2 mmol) and concentrated hydrochloric acid (720 µL) are added to a reaction flask and heated to 100° C. until most of the liquid dissipates from the flask. The temperature of the reaction mixture is then heated to 155° C. for one hour (Example 8A), two hours (Example 8B), three hours (Example 8C) and four hours (Example 8D). The reaction is allowed to cool overnight to room temperature over a flow of nitrogen. The resulting solids are dissolved in 60 mL of distilled water and solution purified by dialysis (100 MWCO tubing) overnight. The purified product is then freeze dried overnight. The $^{13}C$ NMR data for Examples 8A to 8D in Table 10.

TABLE 10

| Example | $M_n$ (GPC) | $M_n$ (NMR) | terminal groups (mol %) | | | in-chain (mol %) | |
|---|---|---|---|---|---|---|---|
| | | | amine | CG | G | GG | G |
| 8A | 1581 | 1593 | 15.4 | 33.8 | 50.7 | 89.6 | 10.4 |
| 8B | 1679 | 1444 | 13.9 | 27.9 | 58.2 | 89.0 | 11.0 |
| 8C | 2036 | 1515 | 10.5 | 32.5 | 57.0 | 88.9 | 11.1 |
| 8D | 2002 | 1437 | 9.5 | 28.1 | 62.3 | 88.5 | 11.5 |

Example 9

An aqueous solution containing sodium dicyanimide (8.9 g), hexamethylene (11.6 g), HMBDA (8.9 g), 36% hydrochloric acid (19 g) and water (7.3 g) is prepared with a pH from 6.5 to 7.5. The solution is heated to 120° C. to remove all of the water. The reaction vessel is then heated to 150° C. and this temperature is maintained for four hours. The reaction is cooled overnight under nitrogen. The resulting solids are dissolved in 60 mL of distilled water and solution purified by dialysis (100 MWCO tubing) overnight. The purified product is then freeze dried overnight. A biguanide product comprising less than 18 mol % of terminal amine groups and 40 mol % and greater of terminal cyanoguanidino groups is obtained as measured by $^{13}C$ NMR.

$^{13}C$ NMR Pulse Sequence and Acquisition Parameters

The resulting polymeric biguanide compositions provided by the Examples above were analyzed by $^{13}C$ NMR (see, below and Table 8) to determine the molar concentration of terminal end groups in each Example. The special pulse technique used to acquire the $^{13}C$ spectra allows one to quantify the relative concentration of each terminal end group, that is, a guanidine, a cyanoguanidino or an amine. The $^{13}C$ NMR data is also used to quantify the relative concentrations of in-chain biguanide groups and in-chain guanide. A representative $^{13}C$ NMR spectrum of one of the polymeric biguanides of the inventioin is shown in FIG. 1. As indicated, the alpha-methylene carbon associated with the terminal amine group is indicated by peak A, the guanidine carbon associated with the terminal guanidine group is indicated by peak B and the guanidine carbon associated with the terminal cyanoguanidino group is indicated by peak C. Also, the carbon associated with the in-chain biguanide is indicated by peak D, and the carbon associated with the in-chain guanide is indicated by peak E.

The samples for $^{13}C$ NMR analysis are prepared using 2.2 ml of polymeric biguanide (20 wt %) in water and 0.3 ml $D_2O$ is added. High-resolution $^{13}C$ NMR is acquired using a Bruker AVANCE 300 MHz spectrometer operating at 75.5 MHz for $^{13}C$ nuclei. For quantitative analysis, spectra are acquired using single-pulse excitation with inverse-gated decoupling for suppression of NOE effects, 1024 transients, and a relaxation delay that is five times longer than the longest $^{13}C$ $T_1$ in the sample. At 300 MHz, the longest $T_1$ observed is 9.0 seconds for the terminal guanidine carbon at ~157 ppm. A relaxation delay of 45 seconds is used to acquire quantitative spectra at 300 MHz. Since $T_1$'s are magnetic field dependent, it will be necessary to run a relaxation experiment if acquiring at a different field strength. All spectra are acquired at 300 K using a 10 mm BBO probe.

I claim:

1. A polymeric biguanide composition comprising less than 18 mol % of terminal amine groups, and 55 mol % or greater of terminal guanidine groups as measured by $^{13}C$ NMR, the composition comprising polymeric biguanides of formula (1) and formula (2)

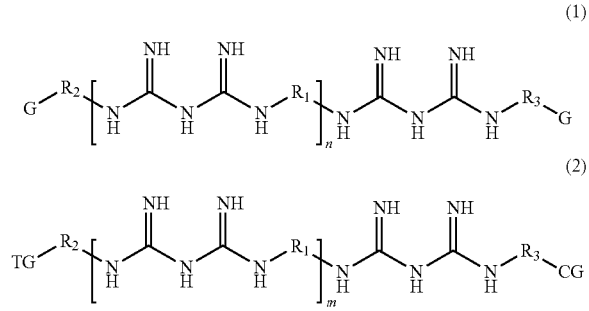

(1)

(2)

wherein the polymeric biguanides of formula (1) and formula (2) account for at least 80 mol % of the total moles of polymeric biguanides in the composition, wherein

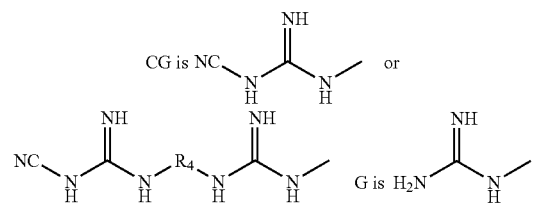

and each TG is the same or different and is selected from CG or G;

$R_1$, $R_2$ and $R_3$ are divalent radicals of an aliphatic hydrocarbon independently selected from the group consisting of a $C_3$-$C_{12}$ alkylene, $C_4$-$C_{12}$ oxyalkylene and $C_4$-$C_{12}$ thioalkylene;

$R_4$ is selected from the group consisting of a $C_2$-$C_{12}$ alkylene, $C_4$-$C_{12}$ oxyalkylene and $C_4$-$C_{12}$ thioalkylene; and n and m represent a number average of repeat units between 1 and 20.

2. The polymeric biguanide composition of claim 1 comprising less than 15 mol % of terminal amine groups, and 60 mol % or greater of terminal guanidine groups.

3. The polymeric biguanide composition of claim 2 comprising 65 mol % or greater of terminal guanidine groups.

4. The polymeric biguanide composition of claim 1 comprising less than 10 mol % of terminal amine groups.

5. The polymeric biguanide composition of claim 1 comprising polymeric biguanides of formula (1), formula (2), formula (3) and optionally formula (4), and having a molar ratio of

[mol % formula (1) +mol % formula (2)]:[mol % formula (3) +mol % formula (4)] from 70:30 or greater

(1)

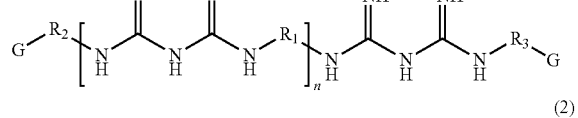

(2)

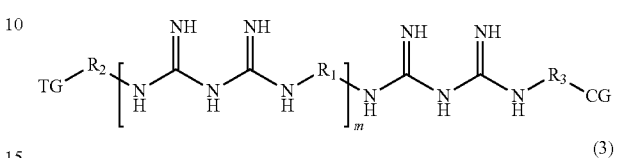

(3)

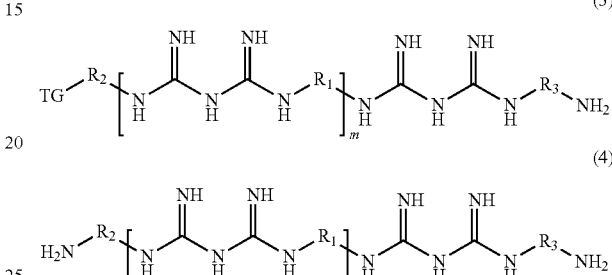

(4)

wherein

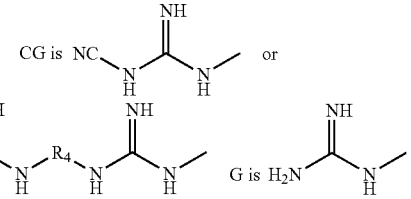

and each TG is the same or different and is selected from CG or G;

$R_1$, $R_2$ and $R_3$ are divalent radicals of an aliphatic hydrocarbon independently selected from the group consisting of a $C_3$-$C_{12}$ alkylene, $C_4$-$C_{12}$ oxyalkylene and $C_4$-$C_{12}$ thioalkylene;

$R_4$ is selected from the group consisting of a $C_2$-$C_{12}$ alkylene, $C_4$-$C_{12}$ oxyalkylene and $C_4$-$C_{12}$ thioalkylene;

n represents a number average of repeat units between 1 and 20; and m is independently selected for each of formulas (2), (3) and (4) and represents a number average of repeat units between 1 and 20.

6. The polymeric biguanide composition of claim 1 wherein the polymeric biguanides of formula (1) and formula (2) account for at least 90 mol % of the total moles of polymeric biguanides.

7. The polymeric biguanide composition of claim 5 wherein n<m.

8. The polymeric biguanide composition of claim 1 wherein n<m.

9. A polymeric biguanide composition comprising less than 18 mol % of terminal amine groups and 40 mol % or greater of terminal cyanoguanidino groups as measured by $^{13}C$ NMR, wherein the composition of polymeric biguanides include formula (1) and formula (2)

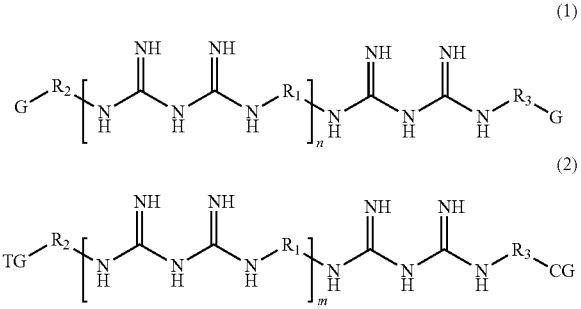

(1)

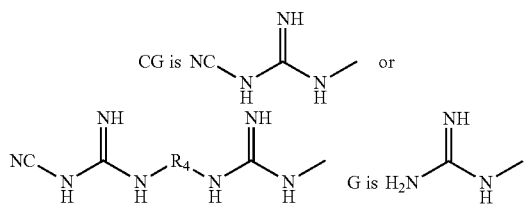

(2)

wherein the polymeric biguanides of formula (1) and formula (2) account for at least 80 mol % of the polymeric biguanides in the composition, wherein

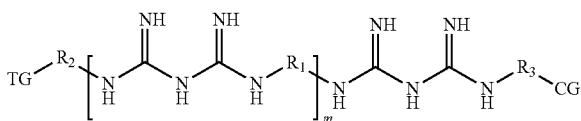

and each TG is the same or different and is selected from CG or G;

$R_1$, R, and $R_3$ are divalent radicals of an aliphatic hydrocarbon independently selected from the group consisting of a $C_3$-$C_{12}$ alkylene, $C_4$-$C_{12}$ oxyalkylene and $C_4$-$C_{12}$ thioalkylene;

$R_4$ is selected from the group consisting of a $C_2$-$C_{12}$ alkylene, $C_4$-$C_{12}$ oxyalkylene and $C_4$-$C_{12}$ thioalkylene; and n and m represent a number average of repeat units between 1 and 20.

10. The polymeric biguanide composition of claim 9 comprising less than 15 mol % of terminal amine groups and 50 mol % or greater of terminal cyanoguanidino groups.

11. The polymeric biguanide composition of claim 9 further comprising from 10 mol % to 30 mol % of terminal guanidine groups.

12. The polymeric biguanide composition of claim 11 comprising 7 to 15 mol % of terminal amine groups and 45 mol% to 70 mol% terminal cyanoguanidino groups.

13. The polymeric biguanide composition of claim 9 further comprising an in-chain biguanide concentration of 90 mol % or greater.

14. An ophthalmic composition comprising one or more cationic antimicrobial components at least one of which is a polymeric biguanide composition that comprises less than 18 mol % of terminal amine groups, and 55 mol % or greater of terminal guanidine groups as measured by $^{13}C$ NMR, the composition comprising polymeric biguanides of formula (1) and formula (2)

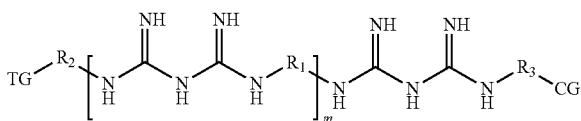

(1)

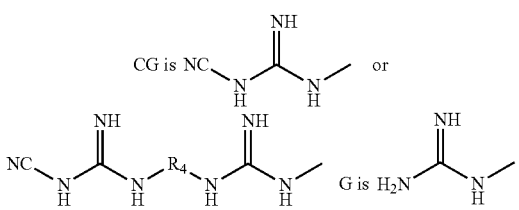

(2)

wherein the polymeric biguanides of formula (1) and formula (2) account for at least 80 mol % of the total moles of polymeric biguanides in the composition, wherein

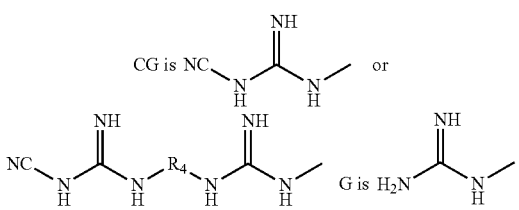

and each TG is the same or different and is selected from CG or G.

$R_1$, $R_2$ and $R_3$ are divalent radicals of an aliphatic hydrocarbon independently selected from the group consisting of a $C_3$-$C_{12}$ alkylene, $C_4$-$C_{12}$ oxyalkylene and $C_4$-$C_{12}$ thioalkylene;

$R_4$ is selected from the group consisting of a $C_2$-$C_{12}$ alkylene, $C_4$-$C_{12}$ oxyalkylene and $C_4$-$C_{12}$ thioalkylene; and n and m represent a number average of repeat units between 1 and 20.

15. The ophthalmic composition of claim 14 wherein the polymeric biguanide composition comprises less than 15 mol % of terminal amine groups and 60 mol % or greater of terminal guanidine groups.

16. The ophthalmic composition of claim 15 wherein the polymeric biguanide composition comprises less than 10 mol % of terminal amine groups.

17. The ophthalmic composition of claim 14 further comprising a cationic antimicrobial component selected from the group consisting of poly[dimethylimino-2-butene-1,4-diyl] chloride, α-[4-tris(2-hydroxyethyl) ammonium chloride-2-butenyl]poly[1-dimethylammonium chloride-2-butenyl]-ω-tris(2-hydroxyethyl)ammonium chloride, myristamidopropyl dimethylamine and mixtures thereof.

18. The ophthalmic composition of claim 14 further comprising dexpanthenol, sorbitol or any combination thereof.

19. An ophthalmic composition comprising one or more cationic antimicrobial components at least one of which is a polymeric biguanide composition that comprises less than 18 mol % of terminal amine groups and 40 mol % or greater of terminal cyanoguanidino groups as measured by $^{13}C$ NMR, wherein the composition of polymeric biguanides include formula (1) and formula (2)

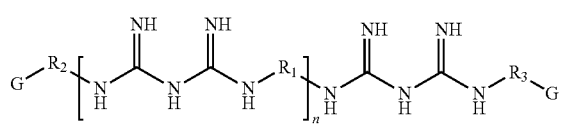

(1)

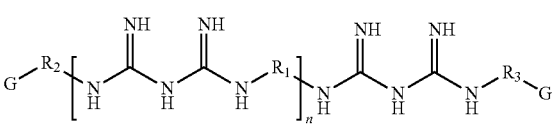

(1)

-continued

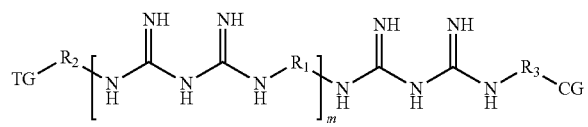
(2)

wherein the polymeric biguanides of formula (1) and formula (2) account for at least 80 mol % of the polymeric biguanides in the composition, wherein

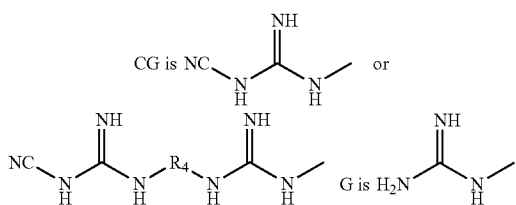

and each TG is the same or different and is selected from CG or G;

$R_1$, $R_2$, and $R_3$ are divalent radicals of an aliphatic hydrocarbon independently selected from the group consisting of a $C_3$-$C_{12}$ alkylene, $C_4$-$C_{12}$ oxyalkylene and $C_4$-$C_{12}$ thioalkylene;

$R_4$ is selected from the group consisting of a $C_2$-$C_{12}$ alkylene, $C_4$-$C_{12}$ oxyalkylene and $C_4$-$C_{12}$ thioalkylene; and n and m represent a number average of repeat units between 1 and 20.

20. The ophthalmic composition of claim 19 wherein the polymeric biguanide composition comprises less than 15 mol % of terminal amine groups and 50 mol % or greater of terminal cyanoguanidino groups.

21. The ophthalmic composition of claim 19 wherein the polymeric biguanide composition comprises from 10 mol % to 30 mol % of terminal guanidine groups.

22. The ophthalmic composition of claim 20 wherein the polymeric biguanide composition comprises 7 to 15mol % of terminal amine groups and 45 mol % to 70 mol % terminal cyanoguanidino groups.

23. The ophthalmic composition of claim 19 further comprising a cationic antimicrobial component selected from the group consisting of poly[dimethylimino-2-butene-1,4-diyl] chloride, α-[4-tris(2-hydroxyethyl) ammonium chloride-2-butenyl]poly[1-dimethylammonium chloride-2-butenyl]-ω-tris(2-hydroxyethyl)ammonium chloride, myristamidopropyl dimethylamine and mixtures thereof.

24. The ophthalmic composition of claim 19 further comprising dexpanthenol, sorbitol or any combination thereof.

* * * * *